US009341622B2

(12) United States Patent
Shiomi et al.

(10) Patent No.: US 9,341,622 B2
(45) Date of Patent: May 17, 2016

(54) CELLULOSE DERIVATIVE FINE PARTICLE, DISPERSION LIQUID THEREOF, DISPERSION BODY THEREOF AND DIAGNOSTIC REAGENT

(71) Applicant: Asahi Kasei Fibers Corporation, Osaka-shi, Osaka (JP)

(72) Inventors: Yoshiyuki Shiomi, Tokyo (JP); Toshihiko Matsui, Tokyo (JP); Masanori Doi, Tokyo (JP)

(73) Assignee: ASAHI KASEI FIBERS CORPORATION, Osaka-Shi (JP)

( * ) Notice: Subject to any disclaimer, the term of this patent is extended or adjusted under 35 U.S.C. 154(b) by 0 days.

(21) Appl. No.: 14/750,970

(22) Filed: Jun. 25, 2015

(65) Prior Publication Data

US 2015/0293082 A1 Oct. 15, 2015

Related U.S. Application Data

(62) Division of application No. 12/935,246, filed as application No. PCT/JP2009/056559 on Mar. 30, 2009, now Pat. No. 9,096,690.

(30) Foreign Application Priority Data

Mar. 31, 2008 (JP) ................................ 2008-090905

(51) Int. Cl.

| | |
|---|---|
| ***G01N 33/544*** | (2006.01) |
| ***G01N 33/548*** | (2006.01) |
| ***C08B 1/00*** | (2006.01) |
| ***C08B 1/08*** | (2006.01) |
| ***C08B 5/14*** | (2006.01) |
| ***C08B 11/02*** | (2006.01) |
| ***C08B 11/04*** | (2006.01) |
| ***C08B 11/08*** | (2006.01) |
| ***C08B 11/10*** | (2006.01) |
| ***C08B 11/12*** | (2006.01) |
| ***C08B 11/145*** | (2006.01) |
| ***C08B 11/155*** | (2006.01) |
| ***C08B 11/20*** | (2006.01) |
| ***C08B 15/00*** | (2006.01) |
| ***C08B 15/04*** | (2006.01) |
| ***C08B 15/10*** | (2006.01) |
| ***C08B 16/00*** | (2006.01) |
| ***C08J 3/16*** | (2006.01) |
| ***C08L 1/08*** | (2006.01) |
| ***C08L 1/26*** | (2006.01) |
| ***C08L 1/28*** | (2006.01) |

(52) U.S. Cl.

CPC .............. *G01N 33/548* (2013.01); *C08B 1/006* (2013.01); *C08B 1/08* (2013.01); *C08B 5/14* (2013.01); *C08B 11/02* (2013.01); *C08B 11/04* (2013.01); *C08B 11/08* (2013.01); *C08B 11/10* (2013.01); *C08B 11/12* (2013.01); *C08B 11/145* (2013.01); *C08B 11/155* (2013.01); *C08B 11/20* (2013.01); *C08B 15/005* (2013.01); *C08B 15/04* (2013.01); *C08B 15/10* (2013.01); *C08B 16/00* (2013.01); *C08J 3/16* (2013.01); *C08L 1/08* (2013.01); *C08L 1/26* (2013.01); *C08L 1/28* (2013.01); *C08L 1/282* (2013.01); *C08L 1/284* (2013.01); *C08L 1/286* (2013.01); *C08L 1/288* (2013.01); *C08J 2301/28* (2013.01); *G01N 2400/26* (2013.01); *Y10T 428/2982* (2015.01)

(58) Field of Classification Search

None

See application file for complete search history.

(56) References Cited

U.S. PATENT DOCUMENTS

| | | | | |
|---|---|---|---|---|
| 4,416,813 | A | 11/1983 | Ikeda et al. | |
| 5,245,024 | A * | 9/1993 | Scarpa et al. | 536/56 |
| 5,747,013 | A | 5/1998 | Mougin et al. | |
| 6,169,130 | B1 | 1/2001 | Bodmeier et al. | |
| 2005/0000388 | A1 | 1/2005 | Cho et al. | |
| 2005/0203278 | A1 | 9/2005 | McCreight et al. | |
| 2006/0219615 | A1 | 10/2006 | Okamoto et al. | |
| 2007/0258975 | A1 | 11/2007 | Hagewiesche et al. | |

(Continued)

FOREIGN PATENT DOCUMENTS

| | | |
|---|---|---|
| GB | 2 246 353 | 1/1992 |
| JP | 57-077625 | 5/1982 |
| JP | 61-211342 | 9/1986 |

(Continued)

OTHER PUBLICATIONS

Changde Zhang et al., "Synthesis and Characterization of a Trifunctional Aminoarnide Cellulose Derivative", Biomacromolecules, 2006, vol. 7, No. 1, p. 139-145.

(Continued)

*Primary Examiner* — Gary W Counts

(74) *Attorney, Agent, or Firm* — Finnegan, Henderson, Farabow, Garrett & Dunner, L.L.P.

(57) ABSTRACT

An object of the present invention is to provide a hydrophilic cellulose derivative fine particle having a small particle size, a dispersion liquid thereof and a dispersion body thereof; and provide a diagnostic reagent composed of the hydrophilic particle, which is excellent in storage stability and does not require excess components, such as an emulsifier or surfactant. The cellulose derivative fine particle of the present invention is a cellulose derivative fine particle comprising a cellulose derivative with a part of hydroxyl groups of cellulose being substituted with a substituent, wherein the average particle diameter is from 9 to 1,000 nm; and the diagnostic reagent of the present invention is a diagnostic reagent obtained by loading a substance differentially interacting with a test object substance on the above-described cellulose derivative fine particle.

3 Claims, 2 Drawing Sheets

(56) References Cited

U.S. PATENT DOCUMENTS

| | | | |
|---|---|---|---|
| 2010/0087552 | A1 | 4/2010 | Shiomi et al. |
| 2011/0245062 | A1 | 10/2011 | Hayakawa |

FOREIGN PATENT DOCUMENTS

| | | | |
|---|---|---|---|
| JP | 63-500893 | A | 3/1988 |
| JP | 04-066532 | | 3/1992 |
| JP | 07-324017 | | 12/1995 |
| JP | 10-068730 | | 3/1998 |
| JP | 2000-355553 | | 12/2000 |
| JP | 2000-355553 | A | 12/2000 |
| JP | 2001-503101 | A | 3/2001 |
| JP | 2005-511797 | A | 4/2005 |
| JP | 2007-528436 | A | 10/2007 |
| JP | 2008-507554 | A | 3/2008 |
| WO | WO 87/01120 | | 2/1987 |
| WO | WO 98/45355 | | 10/1998 |
| WO | WO 2005/090499 | A1 | 9/2005 |
| WO | WO 2006/012500 | A2 | 2/2006 |
| WO | WO 2006-095029 | | 9/2006 |
| WO | WO 2008/084854 | | 7/2008 |

OTHER PUBLICATIONS

Cui, Zhengrong et al., "Chitosan-based Nanoparticles for Topical Genetic Immunization," Journal of Controlled Release, 75 (2001) 409-419.

European Search Report for EP Application No. 09726480.8-2215 dated Aug. 6, 2012.

He, Feng et al., "Stabilization of Fe—Pd Nanoparticles with Sodium Carboxymethyl Cellulose for Enhanced Transport and Dechlorination of Trichlorosthylene In Soli and Groundwater," Ind. Eng. Chem. Res., vol. 46, No. 1, 2007, 29-34.

Hiromitsu Yamamoto et al., "The Development of an Aqueous Polymeric Enteric Coating System with Hydroxypropylmethylcelluiose Phthalate Nanoparticles", J. Soc. Powder Technol., Japan, 1998, vol. 35, No. 6, p. 439-442.

International Search Report from the Japanese Patent Office for International Patent Application No. PCT/JP2009/056659 mailed Jun. 9, 2009.

Meehan, Characterisation of hydroxypropylmethylcellulose phthalate (HPMCP) by GPC using a modified organic solvent, Analytica Chimica Acta 557, 2006, pp. 2-6.

Rath et al., Antibodies generated in Response to Plasmaid DNA Encoding Zone Pellucida Glycoprotgein-B Inhibit in Vitro Human Sperm-Egg Binding, Molecular Reproduction and Development 62, pp. 525-533. 2002.

Spernarth et al., Preparation of ethyl cellulose nanoparticies from nano-emulsion obtained by inversion at constant temperature, Micro & Nano Letters 2007, 2(4), pp. 90-95.

Stephanie Hornig et al., "Efficienit Approach to Design Stable Water-Dispersibie Nanoparticles of Hydrophobic Cellulose Esters", Biomacromolecules, May 2008, vol. 9, No. 5, p. 1487-1492.

Wach, et al., Radiation crosslinking or carboxymethylcelluiose of various degree of substitution at high concentration in aqueous solutions of natural pH, Radiation Physics and Chemistry 68, 2003, pp. 771-779.

Wei Dong et al., "Preparation of HPMC-EA-DMAEMA Nanosized Latex", Cellulose, 2007, vol. 14, No. 4, p. 331-336.

* cited by examiner

CELLULOSE DERIVATIVE FINE PARTICLE, DISPERSION LIQUID THEREOF, DISPERSION BODY THEREOF AND DIAGNOSTIC REAGENT

This is a division of application Ser. No. 12/935,246, §371 Date of Sep. 28, 2010, which is the National Stage of PCT/JP2009/056559, filed Mar. 30, 2009, and claims priority to JP 2008-090905, filed Mar. 31, 2008, all of which are incorporated herein by reference.

TECHNICAL FIELD

The present invention relates to a cellulose fine particle with a part of hydroxyl groups being derivatized, a dispersion liquid thereof, a dispersion body thereof and a diagnostic reagent using the same.

BACKGROUND ART

At present, a large number of polymer fine particles such as nylon, polyethylene, polyacrylonitrile, polystyrene and cellulose are being used in various applications. The number of specific applications is innumerable, but examples thereof include a slipperiness-imparting agent, a toner, a matting agent for coating materials, an additive for light diffusion, an antiblocking agent for packaging materials, an insulating filler, a crystal nucleator, a packing for chromatography, an abrasive and other various additives. Furthermore, in recent years, use as a spacer for liquid crystal display devices, a standard particle for calibration of analyzers, a standard particle for assay on porous film, a carrier for diagnostic reagents, or the like is increasing.

Among these polymer fine particles, cellulose has various characteristics not shared by other synthetic polymers. As for specific examples of the characteristic, cellulose (1) is relatively chemically stable and rarely dissolvable, (2) has heat resistance and is not dissolved even at a high temperature, (3) is an amphiphilic polymer having both water absorbability and oil absorbability, (4) is derived from a natural product and regarded as harmless to human body, (5) has shapability and moldability, (6) rarely causes an interaction with a substance such as protein and causes no adsorption, (7) has many hydroxyl groups and is easy to chemically modify, (8) is easily combusted and does not generate a hazardous substance, and (9) is a biodegradable polymer and regarded as harmless to the environment.

The cellulose fine particle is adopted to a variety of applications by making use of the characteristics (1) to (9) above. The cellulose fine particle has an innumerable number of specific applications and is versatile, for example, as a column packing for various fractionations, an enzyme support, a microorganism culture carrier, a cell culture carrier, a filter element, an adsorbent, a pharmaceutical excipient, a pharmaceutical disintegrant, a pharmaceutical extender, a granulation substrate, a thickening or viscosity adjusting agent for food, a thixotropy-imparting agent, a dispersion stabilizer, a plastic extender, a filler, a base material of cosmetic foundation, a modifier for exterior coating materials, a coating agent, a molding agent for catalyst production by firing, a fiber wall material and a compounding agent for pressure-sensitive copying paper.

Cellulose is a polymer composed of a β-glucose molecule, and three hydroxyl groups present in the β-glucose molecule have a great effect on the characteristics of the polymer. When a part of these hydroxyl groups is converted into another structure, the polymer is called a cellulose derivative. The cellulose derivative has various characteristics according to the kind of the structure substituted, the substitution degree indicative of the extent of substitution, or the like. This cellulose derivative is also used in various applications by making use of its characteristics, similarly to cellulose.

In the past, the present inventors found a cellulose fine particle having both a property that the particle diameter of the fine particle is small and a property that the average polymerization degree of cellulose constituting the fine particle is sufficiently high. It was also found that surprisingly, the cellulose fine particle having a small particle diameter scarcely causes aggregation in water or various mediums even without adding a surfactant and exhibits excellent dispersion stability over a long period of time. This cellulose fine particle is a useful fine particle having the above-described characteristics of cellulose as well as a small particle diameter and may be expected to be applicable to various uses. However, as for the cellulose derivative fine particle having a small particle diameter, only a very limited fine particles are known.

The cellulose derivative fine particle having a small particle diameter, which is known at present, includes those described in Patent Document 1 and Patent Document 2. Both of these fine particles are obtained by previously derivatizing cellulose and molding it into the form of a small nanosize particle. The cellulose is basically not dissolved in water, an organic solvent or a mixture thereof but can be made soluble by derivatization, and molding into a particulate form can be achieved using a solution obtained by dissolving the derivatized cellulose. However, the cellulose derivative fine particle obtained by the method described in these patent publications is basically water-soluble and dissolves in water, and this imposes a strict limitation on the available applications. The cellulose derivative may be considered to become water-insoluble when hydroxyl groups are mostly substituted, but such a cellulose derivative fine particle cannot make use of hydrophilicity that is a characteristic of cellulose. Also in this case, the applications are very limited and furthermore, it may be feared that the fine particle itself causes aggregation in water.

In other words, a cellulose derivative fine particle that has a small particle diameter, does not dissolve even in water and can be present in a stably dispersed state, is not yet known. Such a cellulose derivative fine particle is expected to enjoy expanded usage into various applications, similarly to the cellulose fine particle. One example of these expected applications is a carrier for diagnostic reagents.

The diagnostic reagent indicates a reagent for analyzing a molecule present in the body of a living thing and detecting an abnormality or change in the body. Representative examples of the test using a diagnostic reagent include an immunoserological test, a blood test, cytoscopy and a genetic test. Also, an array used in the test for examining the sequence of an amino acid, such as a peptide array or protein array, may be included in the diagnostic reagent in a broad sense, although the test involves no analysis of a molecule in the body of a living thing. A substance differentially interacting with a substance as the test object is utilized in these tests. Among the tests using a diagnostic reagent, an immunoserological test is most representative, and this test is also called an immunoassay. The immunoassay is a test method utilizing a specific reaction between an antigen and an antibody and aims at detecting a test object substance such as cancer marker, hormone, infection, autoimmunity, plasma protein, TDM or coagulation/fibrinolysis. Such a diagnostic reagent is widely used in practice in the clinical test field because of its simplicity and promptness. Realization of high sensitivity enabling measurement of a tracer amount of a test object substance is demanded at present.

In the diagnostic reagent using a fine particle, a substance differentially interacting with a test object substance is loaded on the fine particle and a change caused when a test object substance is present is detected, thereby effecting the diagnosis. The carrier used for diagnostic reagents is generally a gold nanoparticle called gold colloid or a polystyrene nanoparticle. For example, is an immunochromatography method using a gold nanoparticle described in Patent Document 3 and a latex method using a polystyrene nanoparticle described in Patent Document 4.

However, these nanoparticles are generally hydrophobic and there are, for example, problems that the storage stability is low and fine particles aggregate and precipitate with each other, or nonspecific adsorption of causing an interaction even with a substance other than the test object substance is generated. In some cases, a stabilizer such as surfactant is used for improving the storage stability, but the stabilizer itself gives rise to the nonspecific adsorption. Also, many gold or polystyrene nanoparticles are produced using a reducing agent or an emulsifier in the production step, but such a component remains and causes nonspecific adsorption. In order to solve these various problems, a technique of covering the fine particle surface with a hydrophilic substance by using a blocking agent such as albumin is generally employed. However, the effect of this technique is not sufficient at present. Non-Patent Document 1 describes a technique of thoroughly hydrophilizing the fine particle surface, thereby suppressing nonspecific adsorption, but this technique involves laborious fine particle production and is not streamlined.

In this way, the fine particle for use in the immunoserological test is sometimes required to be a hydrophilic fine particle. Not only in the immunoserological test but also in the general diagnostic reagent field, a hydrophilic fine particle is sometimes required. Also, considering that the proportion of water occupying in the living body is very high and many of molecular reactions in the living body are performed in a water-related environment, a hydrophilic fine particle is anticipated to become useful in biomedical applications. However, the nanoparticle popular at present, such as metal, inorganic material and polymerizable polymer, is usually hydrophobic. In this context, a hydrophilic nanoparticle is demanded not only in the application as a diagnostic reagent but also in various applications.

Patent Document 1: Japanese Unexamined Patent Publication No. 2001-503101

Patent Document 2: Japanese Unexamined Patent Publication No. 2007-528436

Patent Document 3: Japanese Unexamined Patent Publication No. 10-68730

Patent Document 4: Japanese Unexamined Patent Publication No. 2000-355553

Non-Patent Document 1: *Kobunshi Ronbun Shu* (*Collected Papers on Polymer*), Vol. 50, No. 5, pp. 431-435 (May, 1993)

DISCLOSURE OF THE INVENTION

Problems to be Solved by the Invention

Under these circumstances, an object of the present invention is to provide a water-insoluble and hydrophilic cellulose derivative fine particle having a small particle size, a dispersion liquid thereof and a dispersion body thereof. Another object of the present invention is to provide a diagnostic reagent obtained by loading a substance differentially interacting with a test object substance on the above-described cellulose derivative fine particle and thereby assured of excellent properties of having high hydrophilicity and excellent storage stability and not requiring excess components such as emulsifier or surfactant.

Means to Solve the Problems

As a result of intensive studies, the present inventors have succeeded in obtaining a cellulose derivative fine particle having both a property of not dissolving in water and a property of having high hydrophilicity, by derivatizing a part of hydroxyl groups of the cellulose fine particle already reported by the present inventors and described in International Publication No. 2008/084854, pamphlet. Furthermore, it has been found that the cellulose derivative fine particle can also be used as a carrier for diagnostic reagents by utilizing a substituent introduced by derivatization and loading a substance differentially interacting with a test object substance on the cellulose derivative fine particle. The present invention has been accomplished based on these findings. That is, the present invention is as follows.

(1) A cellulose derivative fine particle comprising a cellulose derivative with a part of hydroxyl groups of cellulose being substituted by a substituent, wherein the average particle diameter is from 9 to 1,000 nm.

(2) The cellulose derivative fine particle as described in (1) above, wherein the substitution degree of the substitution is 2.5 or less.

(3) The cellulose derivative fine particle as described in (2) above, wherein the substitution degree of the substitution is 1.0 or less.

(4) The cellulose derivative fine particle as described in any one of (1) to (3) above, wherein the substituent contains any one or more members out of a carboxyl group, an amino group, a quaternary ammonium group, a hydroxyalkyl group, an alkyl group, an acetyl group, a cyanoethyl group, a sulfuric acid group and a crosslinking group that binds at least two or more hydroxyl groups to each other.

(5) The cellulose derivative fine particle as described in any one of (1) to (4) above, wherein a component other than cellulose is loaded through chemical bonding or physical adsorption.

(6) The cellulose derivative fine particle as described in (5) above, wherein the component loaded other than cellulose contains a substance differentially interacting with another component.

(7) The cellulose derivative fine particle as described in (5) or (6) above, wherein the component loaded other than cellulose contains a biomaterial.

(8) The cellulose derivative fine particle as described in (7) above, wherein the biomaterial contains an antigen or an antibody.

(9) A diagnostic reagent containing the cellulose derivative fine particle described in any one of (1) to (8) above.

(10) The diagnostic reagent as described in (9) above, wherein the cellulose derivative fine particle is the cellulose derivative fine particle described in any one of (5) to (8) above and the component loaded other than cellulose contains a substance differentially interacting with a test object substance.

(11) The diagnostic reagent as described in (9) or (10) above, wherein the CV value of the cellulose derivative fine particle is 30% or less.

(12) The diagnostic reagent as described in any one of (9) to (11) above, wherein the diagnosis is an immunoserological diagnosis.

(13) A method for analyte detection, comprising mixing the diagnosis agent described in any one of (9) to (12) above with an analyte and detecting a test object substance in the analyte.

(14) The method for analyte detection as described in (13) above, wherein the diagnostic reagent is the diagnostic reagent described in any one of (10) to (12) above and the test object substance in the analyte is detected by the degree of aggregation of cellulose derivative fine particles.

(15) A dispersion liquid comprising a liquid having dispersed therein the cellulose derivative fine particles described in any one of (1) to (8) above.

(16) A molded body comprising a solid having fixed on the surface thereof or dispersed therein the cellulose derivative fine particles described in any one of (1) to (8) above.

Effects of the Invention

The cellulose derivative fine particle of the present invention is a cellulose derivative fine particle having an unconventionally small particle diameter and further has properties of, for example, having high hydrophilicity and high storage stability and not requiring excess components such as emulsifier or surfactant. Also, by utilizing a substituent of the cellulose derivative and loading a substance differentially interacting with a test object substance on the cellulose derivative fine particle, a diagnostic reagent having excellent features can be provided.

BEST MODE FOR CARRYING OUT THE INVENTION

Figure 1:
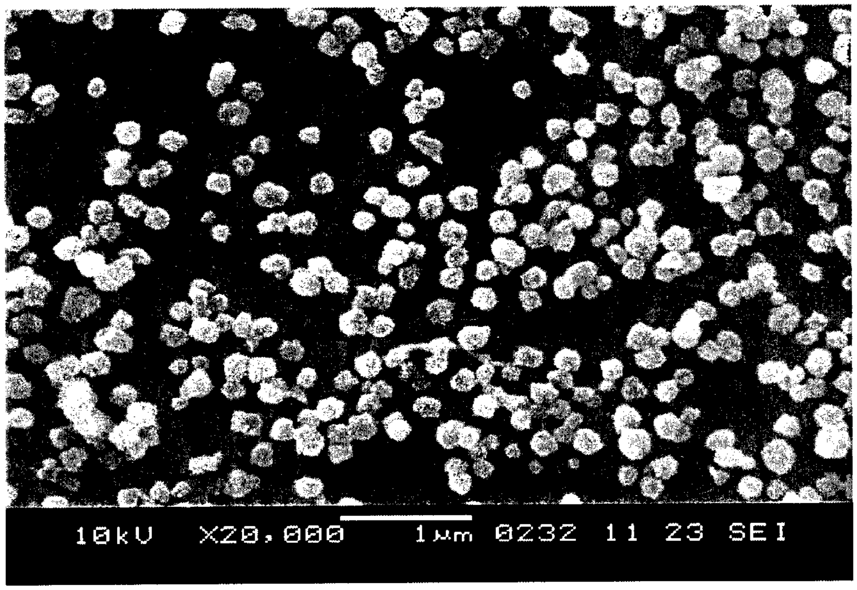
FIG. 1 is an electron micrograph of the carboxylated cellulose fine particle obtained in Example 1, where the photographing magnification is 20,000 times and the scale bar is 1 μm.

The present invention is described in detail below. The cellulose derivative fine particle as used in the present invention indicates a fine particle comprising a cellulose derivative, and the production method thereof is not particularly limited. The cellulose derivative fine particle may be produced by an arbitrary method, for example, by performing derivatization after molding cellulose into a fine particulate form, or by molding a previously derivatized cellulose derivative into a fine particulate form. Of course, the cellulose as a raw material is not particularly limited, and cellulose such as regenerated cellulose, purified cellulose and natural cellulose may be used. In the present invention, cellulose was molded into a fine particulate form by a method of dissolving natural cellulose in a copper ammonia solution, mixing the solution with a coagulating solution to cause microphase separation, and taking out the particle dense phase as a fine particle, and thereafter, derivatization of the fine particle was performed.

The cellulose derivative as used in the present invention indicates a cellulose derivative where a part of hydroxyl groups of cellulose are substituted by another different substituent. The substituent is not particularly limited in its kind, but specific examples thereof include a group containing a substituent such as a carboxyl group, primary, secondary or tertiary amino group, quaternary ammonium group, hydroxyalkyl group, alkyl group, acetyl group, cyanoethyl group, sulfuric acid group, amido group, aldehyde group, nitro group, nitric acid group, tosyl group, phenyl carbanylate group, trityl group and crosslinking group that binds at least two or more hydroxyl groups to each other. Incidentally, the term "crosslinking" as used in the present invention indicates that hydroxyl groups of cellulose are linked together by some compound. The method and kind of the crosslinking are not particularly limited, but, for example, the crosslinking can be performed using a compound having two or more portions reacting with a hydroxyl group, such as epichlorohydrin, formalin, silane coupling agent, epoxy-modified silicone-based crosslinking agent and glyoxal-based resin. In Examples described later, the crosslinking was performed using a glyoxal-based resin or epichlorohydrin. A reactive dye that performs dyeing of cellulose utilizes a reaction with a hydroxyl group and the dye may be said to be one of the substituents. In the case of use of a diagnostic reagent, the substituent preferably contains a carboxyl group or an amino group in view of easy binding to a biomaterial such as an antibody, because, the biomaterial, as well as an antibody, is composed of various amino acids, and an amide bond can be formed with a carboxyl group or amino group of the amino acid. Also, different kinds of substituents may be used in combination, and the substituents may be substituted in various combinations. For example, in the case of using the cellulose derivative fine particle as a diagnostic reagent, for the purpose of modifying the fine particle surface or modifying the degree of swelling, introduction of other substituents or chemical modification, such as crosslinking, may be performed. In the present invention, derivatization was performed by mixing a cellulose fine particle with sodium hydroxide to prepare an alkali cellulose and further adding a reactant. For example, carboxylation can be effected by adding sodium chloroacetate as a reactant and after the completion of reaction, treating the reaction product with hydrochloric acid, and primary amination can be effected by using 2-chloroethylamine as a reactant. Furthermore, amination and crosslinking can be effected at the same time by adding epichlorohydrin as a reactant to perform epoxy activation and then adding aqueous ammonia to cleave the epoxy group. Also, crosslinking can be effected by using a glyoxal-based resin and an appropriate catalyst. By changing the kind of the reactant, various derivatizations can be controlled and various cellulose derivative fine particles can be obtained.

In the present invention, the extent of substitution of the cellulose derivative is expressed by the substitution degree and a higher substitution degree indicates that a larger number of hydroxyl groups are substituted. The substitution degree indicates how many hydroxyl groups are substituted per glucose unit. That is, when three hydroxyl groups all are substituted, the substitution degree is 3; when one hydroxyl group is substituted, the substitution degree is 1; and when hydroxyl groups are not substituted at all, the substitution degree is 0. Incidentally, the substitution degree is just a value obtained by averaging substitution degrees for all glucoses constituting the cellulose.

The substitution degree of the cellulose derivative for use in the present invention is not particularly limited, but in order to be hydrophilic, the substitution degree is preferably 2.5 or less. If the substitution degree is higher than that, hydrophilicity as an object of the present invention may not be achieved. Also, even when the substitution degree is 2.5 or less, the cellulose derivative is water-soluble depending on the kind of the substituent and sometimes becomes difficult to use in water. In such a case, a crosslinked structure may be introduced in addition to the objective substituent. By this introduction, cellulose can be insolubilized in water. The degree of hydrophilicity varies according to the kind of the substitution, the position of the hydroxyl group substituted, or the like and therefore, the substitution degree for ensuring hydrophilicity cannot be indiscriminately specified, but the substitution degree is more preferably 2.0 or less, still more preferably 1.5 or less, yet still more preferably 1.0 or less, and most preferably 0.5 or less.

The average particle diameter as used in the present invention indicates a volumetric median diameter obtained by photographing cellulose derivative fine particles by an electron microscope and image-analyzing the obtained image. The number of fine particles measured is 100 or more. The image photographed by an electron microscope is a planar image and does not necessarily show a stereoscopic shape of the fine particle, but by setting the number of fine particles observed to 100 or more, the stereoscopic shape can be judged in terms of an average value. In this respect, for observing the fine particle by an electron microscope, the particles in the state of being dispersed in a liquid need to be dried. The drying must be carefully performed, because if the fine particles are aggregated during drying, this changes the apparent average particle diameter. In confirming the drying conditions, it is preferred to determine the drying conditions while comparing the particle diameter with that in a never-dry state by using a dynamic light-scattering particle size distribution analyzer. In the present invention, for the drying of fine particles, freeze drying by a metal contact method was used. Also, the value obtained by dividing the standard deviation of the determined volumetric particle diameter distribution by the average particle diameter is a CV value (abbreviation of “Coefficient of Variation”) and is used as an indicator of uniformity of fine particles.

The “fine particle” as used in the present invention indicates a particle having a sufficiently small ratio (major axis/minor axis) between minor axis and major axis of the fine particle in the above-described image analysis of fine particles by an electron microscope. Bar-like, fibrous and net-like particles, in which this ratio is extremely large, are not included in the fine particle. For bringing out the function as a fine particle, with respect to the average value of 100 fine particles, the major axis/short axis is 10.0 or less, preferably 5.0 or less, more preferably 3.0 or less, still more preferably 2.0 or less. As this value is smaller, the shape of the fine particle becomes closer to a true sphere. Also, when the substitution degree of derivatization is excessively high, the obtained fine particle sometimes fails in keeping the particle shape and in the case of drying the particles from the state of fine particles being dispersed in an organic solvent such as IPA, the major axis/minor axis is sufficiently small, but the major axis/minor axis of the fine particle dried from the state of being dispersed in water becomes large in some cases. The particles obtained here are not a fine particle and their use in water incurs a problem.

The reason why an electron microscopic image is used for the measurement of the average particle diameter without using a particle size distribution measurement by dynamic light scattering system is because the cellulose derivative readily swells in water. This is attributable to the fact that the hydrogen bond of cellulose is weakened due to derivatization, and since the extent thereof greatly differs depending on the substitution degree and kind of derivatization, it is difficult to relatively evaluate respective values.

The average particle diameter of the cellulose derivative fine particle of the present invention is from 9 to 1,000 nm, preferably from 9 to 700 nm. When the average particle diameter is in this range, precipitation scarcely occurs during storage for a long time and the fine particle is also suitable for a diagnostic reagent. In the case of use as a diagnostic reagent, the average particle diameter is preferably from 20 to 700 nm. If the average particle diameter is less than 20 nm, aggregation due to bonding with a test object substance can be hardly detected, whereas if the average particle diameter exceeds 700 nm, precipitation of particles readily occurs during storage in a liquid. The average particle diameter is more preferably from 50 to 500 nm. However, for enhancing the sensitivity as a diagnostic reagent, homogenization by classification may be performed. Also, cellulose derivative fine particles having two or more kinds of average particle diameters may be mixed and used.

Whether the cellulose derivative fine particle dissolves in water is affected, for example, by the kind of the substituent, the substitution degree, the position of the hydroxyl group substituted, or the kind of the substance loaded, and the substitution degree cannot be indiscriminately defined. For example, sodium salt-type carboxymethylated cellulose is generally supposed to be water-insoluble with a substitution degree up to 0.4 and be water-soluble with a substitution degree of 0.6 or more. Also, a cellulose derivative with hydroxyl groups at the 2- and 3-positions being preferentially carboxymethylated is supposed to be water-soluble even with a substitution degree of 0.3. Furthermore, methylated cellulose is generally supposed to be water-soluble with a substitution degree of 1.6 to 2.0. In this way, the substitution degree of the water-insoluble cellulose derivative greatly differs depending on various conditions and cannot be indiscriminately specified.

The CV value as used in the present invention is an abbreviation of Coefficient of Variation and is generally used as an indicator of uniformity of fine particles. This value indicates a dispersion degree in the cellulose fine particle dispersion liquid expressed on a volume basis and is defined by the following formula. As this value is smaller, the particle size distribution is sharper and the cellulose fine particles are more uniform in the size. The unit of the value is (%).

CV Value=(standard deviation in the volume particle size distribution determined from an electron microscopic image)/(volume average median diameter determined from the electron microscopic image)×100

The CV value of the cellulose derivative fine particle of the present invention is not particularly specified, but in the case of use as a diagnostic reagent, the value is preferably 30% or less. If the CV value exceeds 30%, this adversely affects the correctness of diagnosis as a diagnostic reagent. The value is more preferably 25% or less, still more preferably 20%. In general, when the CV value is small, correctness of diagnosis is enhanced, but when the CV value becomes too small, a lot of labors and a high cost are involved in the production. In view of the balance between the cost and the correctness, the value is preferably 1% or more.

The cellulose derivative fine particle of the present invention can also be utilized by loading thereon a component other than cellulose through chemical bonding or physical adsorption. Examples of the chemical bonding or physical adsorption include, but are not limited to, covalent bonding, ionic bonding, coordination bonding, metal bonding, hydrogen bonding, hydrophilic adsorption, hydrophobic adsorption and van der Waals bonding. A component other than cellulose is loaded on the cellulose derivative fine particle by these various forces, whereby a fine particle having a function that the cellulose derivative does not have can be prepared. A component other than cellulose can be loaded even on a cellulose fine particle where the cellulose is not derivatized, but by arbitrarily varying the kind of the substituent, a larger number of kinds of components can be loaded.

The component loaded on the cellulose derivative fine particle of the present invention indicates various substances other than a cellulose derivative and is not particularly limited in its kind. Examples thereof include, but are not limited to, a surfactant, an inorganic fine particle, an organic fine particle, a biomaterial, a dye, an ionic substance, a water-soluble low molecule and a blocking agent.

The biomaterial loaded on the cellulose derivative of the present invention indicates various materials obtained from a living body and is not particularly limited in its kind. Examples thereof include collagen, gelatin, fibroin, heparin, hyaluronic acid, starch, chitin, chitosan, amino acid, peptide, protein, nucleic acid, carbohydrate, fatty acid, terpenoid, carotenoid, tetrapyrrole, cofactor, steroid, flavonoid, alkanoid, polyketide, glycoside, enzyme, antibody and antigen. When such a biomaterial is loaded, this enables enhancement of biocompatibility of the cellulose derivative fine particle, utilization as a diagnostic reagent, and the like.

In the present invention, the cellulose derivative fine particle can be used as a diagnostic reagent by loading a substance differentially binding to a test object substance on the cellulose derivative fine particle.

The test object substance as used in the present invention indicates an object of measurement, for example, in a test such as immunoserological test, blood test, cytoscopy and genetic test and is not particularly limited in its kind. Examples thereof include cancer marker, hormone, infection, autoimmunity, plasma protein, TDM, coagulation/fibrinolysis, amino acid, peptide, protein, gene and cell. Specific examples thereof include CEA, AFP, ferritirin, β2 microglubulin, PSA, CA19-9, CAl25, BFP, esterase 1, pepsinogen 1•2, fecal occult blood, urinary β2 microglubulin, PIVKA-2, urinary BTA, insulin, E3, HCG, HPL, LH, HCV antigen, HBs antigen, HBs antibody, HBc antibody, Hbe antigen, Hbe antibody, HTLV-1 antibody, HIV antibody, toxoplasma antibody, syphilis, ASO, A-type influenza antigen, A-type influenza antibody, B-type influenza antigen, B-type influenza antibody, rotavirus antigen, adenovirus antigen, rotavirus/adenovirus antigen, group A *Streptococcus*, group B *Streptococcus, Candida* antigen, CD strain, *Cryptococcus* antigen, *Vibrio cholerae, meningococcus* antigen, granulocytic elastase, *Helicobacter pylori* antibody, O157 antibody, O157 antigen, leptospiral antibody, *Aspergillus* antigen, MRSA, RF, total IgE, LE test, CRP, IgG, IgA, IgM, IgD, transferrin, urinary albumin, urinary transferrin, myoglobin, C3/C4, SAA, LP(a), α1-AC, α1-M, haptoglobin, microtransferrin, APR score, FDP, D dimer, plasminogen, AT3, α2PI, PIC, PAI-1, protein C, coagulation factor X3, type IV collagen, hyaluronic acid, GHbA1c, various antigens, various antibodies, various viruses, various strains, various amino acids, various peptides, various proteins, various DNAs and various cells.

The substance differentially interacting with a test object substance as used in the present invention indicates a substance that selectively adsorbs or binds to the test object substance, and the kind thereof is not particularly limited. Examples thereof include an antigen, an antibody, an amino acid, peptide, protein and a base sequence. In particular, when an antibody is used, presence of various antigens in the immunoserological test can be detected. For example, in the case of using an antibody, the source thereof is not particularly limited and either a polyclonal antibody or a monoclonal antibody may be used. Furthermore, the binding mode of the loaded substance is also not particularly limited and may be either physical adsorption or chemical bonding. Considering the labor when loading the substance, physical adsorption is preferred, and in view of stability after loading, chemical bonding is preferred.

In the present invention, when using the cellulose derivative fine particle as a diagnostic reagent, the loading amount of the substance loaded cannot be indiscriminately specified. The substance loaded can be used by appropriately adjusting the loading amount according to various conditions such as kind, size and abundance in analyte of the test object substance, kind and size of the substance loaded, and size, substitution degree and kind of substituent of the cellulose derivative fine particle on which the substance is loaded.

In the present invention, when the cellulose derivative fine particle is used as a diagnostic reagent, the diagnosis can be performed by detecting a change caused due to the presence of a test object substance. Various changes are detected according to the measurement principle, and various changes such as turbidity, color, particle diameter, potential, absorbance, light transmittance and interaction with other substances can be used for the measurement. Also, the method for detecting the change may be selected according to respective changes, and, for example, readout using a device or judgement with an eye may be utilized. In the present invention, as described later, the change of absorbance at a specific wavelength was measured using an ultraviolet-visible spectrophotometer.

In measuring the change of absorbance at a specific wavelength by using an ultraviolet-visible spectrophotometer, the cellulose derivative fine particle as a diagnostic reagent and an analyte are mixed, and the test object substance in the analyte can be quantitatively determined by the degree of aggregation of cellulose derivative fine particles. In this detection method, preferred requirements are that the cellulose derivative fine particle is a fine particle having a specific nanosize particle diameter, is hydrophilic, scarcely aggregates, is stably dispersed and is uniform in the particle size of fine particles. When these requirements are satisfied, the test object substance can be detected with high accuracy and no variation. In particular, when a cellulose derivative fine particle having a small CV value is used, the amount of the test object substance and the change of the particle diameter are more homogenized and more correct measurement as a diagnostic reagent can be realized. The CV value is preferably 30% or less, more preferably 25% or less, still more preferably 20% or less.

In the present invention, in using the cellulose derivative fine particle as a diagnostic reagent, the fine particle can be used by dispersing the cellulose derivative fine particles in various solutions but is preferably dispersed in a buffer solution at a pH of 5.0 to 9.0. Examples of the buffer solution include a phosphate buffer solution, a glycine buffer solution, a tris buffer solution, a borate buffer solution, a citrate buffer solution and an MES buffer solution. The concentration of the buffer solution is not particularly limited, and various concentrations generally employed as a buffer solution may be used. The concentration of the cellulose derivative fine particle in the solution is also not particularly limited and may be appropriately adjusted according to the kind, property, concentration and the like of the test object substance. In general, the concentration is preferably on the order of 0.01 to 10 wt %, more preferably from 0.1 to 1.0 wt %.

In the present invention, when using the cellulose derivative fine particle as a diagnostic reagent, various sensitizers may be used for enhancing the measurement sensitivity or promoting the antigen-antibody reaction. Also, a blocking agent or the like may be used for inhibiting unspecific adsorption that is caused by other substances present in the analyte.

The cellulose derivative fine particle of the present invention may also be used like a diagnostic reagent by dispersing it in an arbitrary liquid. Furthermore, for example, the fine particle may be used by dispersing it in an arbitrary solid or by fixing it on a solid surface. The cellulose derivative fine particle may also be colored so that visibility of the fine particle can be enhanced or the detection sensitivity can be raised.

In addition, when the cellulose derivative fine particle of the present invention is added alone in a conventional diagnostic reagent, this is expected to produce an effect such as enhancement of stability of reagent, elevation of measurement sensitivity or reduction of reaction time, by making use of hydrophilicity and stability of cellulose.

While the case of loading a substance differentially interacting with other components is described in detail by referring to a diagnostic reagent as an example, the present invention can be applied also to an adsorbent, a sustained preparation, a column carrier and the like.

EXAMPLES

The present invention is described in greater detail below by referring to Examples, but the present invention is not limited only to these Examples. Unless otherwise indicated, all operations were performed in an environment of 25° C.

<Dispersion Treatment by High-Pressure Homogenizer>

A hydraulic ultrahigh pressure homogenizer, M-110-E/H, manufactured by Microfluidics Corporation was used. At this time, the treating pressure was 50 MPa, and an operation of passing the sample through a chamber that is a high-pressure part was performed 10 times.

<Measurement of Average Particle Diameter>

The cellulose fine particles were observed using the following two kinds of electron microscopes according to the magnification required. A transmission electron microscope, JEM2000EX, manufactured by JEOL Ltd. (observed with an accelerating voltage of 100 kV at a magnification of 50,000 times or 100,000 times) and a scanning electron microscope, JSM-6380, manufactured by JEOL Ltd. (observed with an accelerating voltage of 10 kV at a magnification of 20,000 times) were used. As for the drying from a cellulose derivative fine particle dispersion liquid to a powdered cellulose derivative fine particle, unless otherwise indicated, freeze reduced-pressure drying was performed by rapidly freezing the cellulose derivative fine particle dispersion liquid with liquefied nitrogen and reducing the pressure.

An image obtained as above was analyzed using an image analysis-type particle size distribution measurement software, Mac-View, Ver. 3, produced by Mountech Co., Ltd. The number of fine particles measured was set to 100 or more for ensuring accuracy and in the case where the number of particles present in one image is less than 100, two or more images were analyzed.

<Confirmation of Carboxylation of Cellulose Fine Particle>

A powdered carboxylated cellulose fine particles was prepared by the same method as above and measured for the 1H-nuclear magnetic resonance spectrum by using a nuclear magnetic resonance measuring apparatus, JNM-ECA400, manufactured by JEOL Ltd. The ratio of integration values of the proton bound to C1 of the cellulose skeleton and the methylene proton of the carboxylmethyl group was read from the spectrum, and the substitution degree was calculated. The measurement was performed under the following conditions.

Measurement solvent: a 11 wt % deuterated sodium hydroxide solution (prepared from heavy water and deuterated sodium hydroxide)

Appearance position of C1 proton: 4.13 ppm

Appearance position of methylene proton: 3.37 ppm, 3.65 ppm

<Confirmation of Amination of Cellulose Fine Particle>

An analysis according to the Kjeldahl method was performed by a conventionally known method and after quantitatively determining the amount of nitrogen contained in the aminated cellulose fine particle, the substitution degree was calculated from the molecular weight of the aminated cellulose. However, in the case where a crosslinked structure was contained and the molecular weight could not be defined, calculation of the substitution degree is impossible and was not performed.

<Confirmation of Other Derivatizations of Cellulose Fine Particle>

Similarly to the confirmation of carboxylation above, the substitution degree was calculated by comparing the integration value of the appearance positions according to respective substituents with that of the appearance position of C1 proton.

<Confirmation of Crosslinking of Cellulose Fine Particle>

The weight of the cellulose fine particle before crosslinking and the weight of the cellulose fine particle after crosslinking were measured, and the substitution degree of crosslinking was calculated from the value of increase in weight.

<Evaluation of Performance as Diagnostic Reagent>

Measurement was performed using an ultraviolet-visible spectrophotometer (V-630, manufactured by JASCO Corporation). The measurement was performed under the following conditions.

Analyte: 3.0 μl

Dilute solution: 160 μl

Amount of diagnostic reagent: 40 μl

Measurement wavelength: 600 nm

Measurement point: The value of change of absorbance was measured immediately after mixing with an analyte and after 5 minutes.

Reaction temperature: 37° C.

<Explanation of Reagents, etc. Used in Examples>

Acetone: produced by Wako Pure Chemical Industries, Ltd., guaranteed

Isopropyl alcohol: produced by Kishida Chemical Co., Ltd., guaranteed

Dimethylsulfoxide: produced by Wako Pure Chemical Industries, Ltd., guaranteed

Tetrahydrofuran: produced by Wako Pure Chemical Industries, Ltd., guaranteed

Sodium chloroacetate: produced by Wako Pure Chemical Industries, Ltd.

2-Chloroethylamine hydrochloride: produced by Wako Pure Chemical Industries, Ltd.

Epichlorohydrin: produced by Wako Pure Chemical Industries, Ltd.

2-Morpholinoethanesulfonic acid (for MES buffer solution): produced by Dojindo Laboratories Disodium phosphate 12 hydrate (for phosphate buffer solution): produced by Wako Pure Chemical Industries, Ltd.

Potassium dihydrogenphosphate (for phosphate buffer solution): produced by Wako Pure Chemical Industries, Ltd.

2-Amino-2-(hydroxymethyl)propane-1,3-diol hydrochloride (for Tris buffer solution): produced by Merck 1-Ethyl-3-(3-dimethylaminopropyl)carbodiimide hydrochloride (EDC): produced by Dojindo Laboratories Anti-CRP antibody: produced by Wako Pure Chemical Industries, Ltd., Anti Human CRP monoclonal antibody CRP Antigen: produced by Wako Pure Chemical Industries, Ltd., LT-CRP-HS calibrator set T (5 kinds of antigen concentrations: 0.4, 1.2, 3.5, 16.0 and 35.0 mg/dl)

For others, unless otherwise indicated in Examples, reagents produced by Wako Pure Chemical Industries, Ltd. were used.

Example 1

A copper ammonia cellulose solution having a cellulose concentration of 0.37 wt %, a copper concentration of 0.13 wt % and an ammonia concentration of 1.00 wt % was prepared by a conventionally known method. Furthermore, a coagulating solution having a tetrahydrofuran concentration of 89.0 wt % and a water concentration of 11.0 wt % was prepared.

While slowly stirring 5,000 g of the coagulating solution with a magnetic stirrer, 500 g of the copper ammonia cellulose solution prepared above was added. After continuing stirring for about 5 seconds, 1,000 g of 10 wt % sulfuric acid was added to effect neutralization and regeneration, whereby 6,500 g of a slurry containing cellulose fine particles was obtained.

The obtained slurry was centrifuged at a speed of 10,000 rpm for 10 minutes. The precipitate was taken out by decantation, deionized water was poured and after stirring, the mixture was again centrifuged. This operation was repeated several times until the pH became from 6.0 to 7.0, and thereafter, a dispersion treatment by a high-pressure homogenizer was performed to obtain 150 g of a cellulose fine particle dispersion liquid. The average particle diameter of the obtained cellulose fine particles was measured and found to be 261 nm. Also, the CV value thereof was 18%.

Pure water and isopropyl alcohol were added to a part of the obtained cellulose fine particle dispersion liquid, thereby adjusting such that the ratio of isopropyl alcohol:water as the dispersion medium became 85:15 and the particle concentration in the dispersion medium became 0.20 wt %, to prepare 100 g of a cellulose fine particle dispersion liquid (cellulose portion: 0.2 g). The cellulose fine particle dispersion liquid was put into a Kjeldahl flask together with a rotor, and a glass-made reflux tube was attached to the flask. The flask was heated in a water bath for 30 minutes to allow the cellulose fine particle dispersion liquid to reach 50° C. while cooling by refluxing tap water at about 10° C. Here, the heating was performed with gentle stirring by using the magnetic stirrer. Furthermore, a 11% sodium hydroxide solution was prepared, and 0.54 g of the sodium hydroxide solution (molar ratio of cellulose:sodium hydroxide=1.0:1.2) was added to the cellulose fine particle dispersion liquid with stirring. The stirring was continued for 30 minutes, whereby alkali cellulose was prepared. After the preparation of alkali cellulose, 70 mg of sodium chloroacetate (molar ratio of cellulose:sodium chloroacetate=1.0:0.5) was added while further continuing the stirring.

Stirring and refluxing were continued for 3 hours to effect carboxylation of cellulose. After a lapse of 3 hours, heating by a water bath was stopped and the Kjeldahl flack was cooled with ice water until the slurry after reaction reached a temperature of 20° C. Subsequently to the cooling, 5.0 g of 10% hydrochloric acid was added while continuing stirring to make acidic the pH of the slurry after reaction. Decantation and dilution with deionized water were repeated several times using a centrifugal separator in the same manner as above to adjust the pH to 6.0 to 7.0, and a dispersion treatment by a high-pressure homogenizer was further performed to obtain 100 g of a carboxylated cellulose fine particle dispersion liquid. The average particle diameter of the carboxylated cellulose fine particles obtained was measured and found to be 264 nm. The CV value thereof was 19%. FIG. 1 shows an electron micrograph of the fine particles. Furthermore, the substitution degree was calculated using a nuclear magnetic resonance measuring apparatus, as a result, the substitution degree was 0.078.

Example 2

Using the cellulose fine particle dispersion liquid having an average particle diameter of 261 nm prepared in Example 1, carboxylation of cellulose was effected in the same manner as in Example 1 except that the amount of sodium chloroacetate added was 140 mg (molar ratio of cellulose:sodium chloroacetate=1.0:1.0). The average particle diameter of the carboxylated cellulose fine particles obtained was measured and found to be 263 nm. The CV value thereof was 21%. The substitution degree was 0.157.

Example 3

Using the cellulose fine particle dispersion liquid having an average particle diameter of 261 nm prepared in Example 1, carboxylation of cellulose was effected in the same manner as in Example 1 except that the amount of sodium chloroacetate added was 280 mg (molar ratio of cellulose:sodium chloroacetate=1.0:2.0). The average particle diameter of the carboxylated cellulose fine particles obtained was measured and found to be 266 nm. The CV value thereof was 22%. The substitution degree was 0.312.

Example 4

Using the cellulose fine particle dispersion liquid having an average particle diameter of 261 nm prepared in Example 1, carboxylation of cellulose was effected in the same manner as in Example 1 except that the amount of sodium chloroacetate added was 560 mg (molar ratio of cellulose:sodium chloroacetate=1.0:4.0). The average particle diameter of the carboxylated cellulose fine particles obtained was measured and found to be 269 nm. The CV value thereof was 22%. The substitution degree was 0.486.

Comparative Example 1

Using the cellulose fine particle dispersion liquid having an average particle diameter of 261 nm prepared in Example 1, carboxylation of cellulose was effected in the same manner as in Example 1 except that the amount of sodium chloroacetate added was 700 mg (molar ratio of cellulose:sodium chloroacetate=1.0:5.0). An electron microscopic image was photographed to measure the average particle diameter of the carboxylated cellulose fine particles obtained, as a result, it was confirmed that the particle had a net-like structure. The substitution degree was 0.540.

In the case where the cellulose derivative is carboxylated cellulose, the cellulose derivative was easily dissolved in water with a substitution degree of 0.54 and could not keep the particle shape.

Comparative Example 2

Using the cellulose fine particle dispersion liquid having an average particle diameter of 261 nm prepared in Example 1, carboxylation of cellulose was effected in the same manner as in Example 1 except that the amount of 11% sodium hydroxide added was 4.50 g (molar ratio of cellulose:sodium hydroxide=1.0:10.0) and the amount of sodium chloroacetate added was 7.0 g (molar ratio of cellulose:sodium chloroacetate=1.0:50.0). After the completion of reaction, water washing using a centrifugal separator was attempted, but the carboxylated cellulose produced was dissolved out in 85% isopropyl alcohol (15% was water) as the reaction solvent and could not be collected.

Example 5

Cellulose fine particles having an average particle diameter of 9.2 nm and a CV value of 20% were obtained in the same manner as in Example 1 except that the ammonia concentration of the copper ammonia cellulose solution was 6.3 wt % and the coagulating solution was isopropyl alcohol. Furthermore, carboxylation of cellulose was effected in the same manner as in Example 3 to obtain carboxylated cellulose fine particles having an average particle diameter of 9.8 nm, a CV value of 20% and a substitution degree of 0.320.

Example 6

Cellulose fine particles having an average particle diameter of 521 nm and a CV value of 26% were obtained in the same manner as in Example 1 except that the ammonia concentration of the copper ammonia cellulose solution was 8.5 wt % and the coagulating solution was composed of 90.0 wt % of tetrahydrofuran and 10.0 wt % of water. Furthermore, carboxylation of cellulose was effected in the same manner as in Example 1 to obtain carboxylated cellulose fine particles having an average particle diameter of 524 nm, a CV value of 28% and a substitution degree of 0.151.

Comparative Example 3

Cellulose fine particles having an average particle diameter of 5,121 nm and a CV value of 10% were obtained by a spray dry process in accordance with the conventionally known method. Furthermore, carboxylation of cellulose was effected in the same manner as in Example 3 to obtain carboxylated cellulose fine particles having an average particle diameter of 5,020 nm, a CV value of 11% and a substitution degree of 0.325.

As apparent from Examples 1 to 6 and Comparative Examples 1 to 3, the substitution degree of carboxylation was Example 1<Example 2<Example 3<Example 4<Comparative Example 1<Comparative Example 2, and the substitution degree could be controlled according to the amount of sodium hydroxide used or the amount of reactant used. Also, derivatization could be effected in the same manner even when the size of the cellulose fine particle used was changed.

Example 7

The cellulose fine particle dispersion liquid having an average particle diameter of 261 nm prepared in Example 1 was dispersed in pure water, thereby adjusting the particle concentration in water to 1.0 wt %, to prepare 20 g of a cellulose fine particle dispersion liquid (cellulose portion: 0.2 g). Thereafter, in the same manner as in Example 1, the temperature was controlled to 50° C., sodium hydroxide was added with stirring, the sodium hydroxide concentration in water was adjusted to 9.0 wt %, and stirring was continued for 30 minutes. Furthermore, 430 mg of 2-chloroethylamine hydrochloride (molar ratio of cellulose:2-chloroethylamine hydrochloride=1.0:3.0) was added. Stirring and refluxing were continued for 3 hours to effect primary amination of cellulose. After a lapse of 3 hours, the same operation as in Example 1 was performed to obtain 100 g of a primary aminated cellulose fine particle dispersion liquid. The primary aminated cellulose fine particles obtained had an average particle diameter of 259 nm, a CV value of 19% and a substitution degree of 0.099.

Example 8

100 Gram of a primary aminated cellulose fine particle dispersion liquid was obtained in the same manner as in Example 7 except that the amount of 2-chloroethylamine hydrochloride used was changed to 1.43 g (molar ratio of cellulose:2-chloroethylamine hydrochloride=1.0:10.0). The primary aminated cellulose fine particles obtained had an average particle diameter of 270 nm, a CV value of 18% and a substitution degree of 0.209.

Example 9

100 Gram of a primary aminated cellulose fine particle dispersion liquid was obtained in the same manner as in Example 7 except that the amount of 2-chloroethylamine hydrochloride used was changed to 7.16 g (molar ratio of cellulose:2-chloroethylamine hydrochloride=1.0:30.0). The primary aminated cellulose fine particles obtained had an average particle diameter of 268 nm, a CV value of 21% and a substitution degree of 0.323.

Example 10

Quaternary aminated cellulose fine particles were obtained in the same manner as in Example 7 except that the reactant used was changed to 9.56 g of 2-chloroethyltrimethylammonium chloride (molar ratio of cellulose:2-chloroethyltrimethylammonium chloride=1.0:50.0). The quaternary aminated cellulose fine particles obtained had an average particle diameter of 265 nm, a CV value of 22% and a substitution degree of 0.178. Also, the amount of the reactant used was changed in the same manner as in Examples 7 to 9, as a result, it was confirmed that the substitution degree can be controlled according to the amount of the reactant used.

Example 11

Hydroxyethylated cellulose fine particles were obtained in the same manner as in Example 7 except that the reactant used was changed to 4.97 g of 2-chloroethanol (molar ratio of cellulose:2-chloroethanol=1.0:50.0). The hydroxyethylated cellulose fine particles obtained had an average particle diameter of 263 nm, a CV value of 24% and a substitution degree of 0.257. Here, calculation of the substitution degree was performed using NMR. Also, the amount of the reactant used was changed in the same manner as in Examples 7 to 9, as a result, it was confirmed that the substitution degree can be controlled according to the amount of the reactant used.

Example 12

Using the cellulose fine particle dispersion liquid of 261 nm prepared in Example 1, 100 g of a methylated cellulose fine particle dispersion liquid was obtained in the same manner as in Example 1 except that the amount of the 11% sodium hydroxide solution used was changed to 2.25 g (molar ratio of cellulose:sodium hydroxide=1.0:5.0) and 17.5 g of methyl iodide (molar ratio of cellulose:methyl iodide=1.0:100.0) was used as the reactant in place of sodium chloroacetate. The methylated cellulose fine particles obtained had an average particle diameter of 264 nm, a CV value of 20% and a substitution degree of 0.972. Here, calculation of the substitution degree was performed using NMR. Also, the amount of the reactant used was changed in the same manner as in Examples 7 to 9, as a result, it was confirmed that the substitution degree can be controlled according to the amount of the reactant used.

Example 13

An ethylated cellulose fine particle dispersion liquid was obtained in the same manner as in Example 12 except that the reactant used was changed to 6.73 g of bromoethane (molar ratio of cellulose:bromoethane=1.0:50.0). The ethylated cellulose fine particles obtained had an average particle diameter of 251 nm, a CV value of 20% and a substitution degree of 0.745. Here, calculation of the substitution degree was performed using NMR. Also, the amount of the reactant used was changed in the same manner as in Examples 7 to 9, as a result, it was confirmed that the substitution degree can be controlled according to the amount of the reactant used.

As apparent from Examples 7 to 13, the kind of the substituent could be changed by changing the reactant used.

Example 14

The cellulose fine particle dispersion liquid having an average particle diameter of 261 nm prepared in Example 1 was dispersed in pure water, thereby adjusting the particle concentration in water to 10.0 wt %, to prepare 100 g of a cellulose fine particle dispersion liquid (cellulose portion: 10 g). Thereafter, 50 g of a glyoxal-based resin processing agent "BECKAMINE LF-X" (produced by DIC Corporation) and 15 g of a magnesium chloride-based catalyst "Catalyst M" (produced by DIC Corporation) were added while stirring the obtained dispersion liquid with a magnetic stirrer and performing reflux in an environment of 80° C., and stirring was continued for 30 minutes to effect crosslinking of the cellulose fine particle. For the resulting crosslinked cellulose fine particle dispersion liquid, decantation and dilution with deionized water were repeated three times using a centrifugal separator in the same manner as in Example 1 to obtain a crosslinked cellulose fine particle dispersion liquid. The ratio of the crosslinked substituent was calculated from the change in weight of cellulose. The ratio of the crosslinked hydroxyl group was 0.32 in terms of the substitution degree. Carboxylation of the crosslinked cellulose fine particle obtained was performed in the same manner as in Comparative Example 2, as a result, fine particles could be collected by a treatment in a centrifugal separator and carboxylated and crosslinked cellulose derivative fine particles were obtained. The carboxylated and crosslinked cellulose derivative fine particles obtained had an average particle diameter of 275 nm and a CV value of 23%. Also, since the carboxylated and crosslinked cellulose derivative fine particles obtained could not be dissolved in a 11% deuterated sodium hydroxide solution, neutralization titration was performed with a 0.1% sodium hydroxide solution and the substitution degree of carboxylation was calculated from the amount of the 0.1% sodium hydroxide solution used when the pH of the solution became 7.0, as a result, the substitution degree of carboxylation was 2.13.

As seen from comparison between Comparative Example 2 and this Example, a fine particle having a high substitution degree of carboxylation but being insoluble in water could be successfully obtained by adding a crosslinked structure to carboxylation.

Example 15

A cellulose fine particle dispersion liquid was prepared by adjusting the cellulose particle concentration to 1.0 wt % and the sodium hydroxide concentration to 9.0 wt % in the same manner as in Example 7, and 2.28 g of epichlorohydrin (molar ratio of cellulose:epichlorohydrin=1.0:20.0) was added as a reactant.

Stirring and refluxing were continued for 3 hours to effect epoxy activation of the hydroxyl group of cellulose. After a lapse of 3 hours, 9.14 g of 23 wt % aqueous ammonia (molar ratio of cellulose:ammonia=1.0:100.0) was further added to cleave the epoxy group with ammonia, thereby effecting primary amination and crosslinking. After the completion of reaction, water washing was performed in the same manner as in Example 7 to obtain 100 g of an aminated cellulose fine particle dispersion liquid. The average particle diameter of the aminated cellulose fine particles obtained was measured and found to be 270 nm. The CV value thereof was 20%. Furthermore, the nitrogen portion contained in the aminated cellulose was quantitatively determined by the Kjeldahl method and found to be 1.21%. Also, the amount of the reactant used was changed in the same manner as in Examples 7 to 9, as a result, it was confirmed that the nitrogen portion can be controlled according to the amount of the reactant used. In this way, it was verified that crosslinking and amination can be performed at the same time by using epichlorohydrin.

The kind of substituent, substitution degree, average particle diameter, CV value and fine particle shape observed from an electron microscopic image of each of the cellulose derivative fine particles obtained in Examples 1 to 15 and Comparative Examples 1 to 3 are shown together in Table 1. Also, the cellulose fine particles before derivatization, obtained in the middle of process of Examples 1, 5 and 6, are designated as Comparative Examples 4 to 6, respectively, and the average particle diameter, CV value and fine particle shape thereof are shown together in Table 1.

TABLE 1

| | Kind of Derivatization | Substitution Degree | Average Particle Size | CV Value | Shape of Fine particle |
|---|---|---|---|---|---|
| Example 1 | carboxylation | 0.078 | 264 nm | 19% | almost spherical |
| Example 2 | carboxylation | 0.157 | 263 nm | 21% | almost spherical |
| Example 3 | carboxylation | 0.312 | 266 nm | 22% | almost spherical |
| Example 4 | carboxylation | 0.486 | 269 nm | 22% | almost spherical |
| Comparative Example 1 | carboxylation | 0.540 | could not be calculated | | net-like |
| Comparative Example 2 | carboxylation | could not be measured | could not be calculated | | dissolved |
| Example 5 | carboxylation | 0.320 | 9.8 nm | 20% | almost spherical |
| Example 6 | carboxylation | 0.151 | 524 nm | 28% | almost spherical |
| Comparative Example 3 | carboxylation | 0.325 | 5020 nm | 11% | spherical |
| Example 7 | primary amination | 0.099 | 259 nm | 19% | almost spherical |

TABLE 1-continued

| | Kind of Derivatization | Substitution Degree | Average Particle Size | CV Value | Shape of Fine particle |
|---|---|---|---|---|---|
| Example 8 | primary amination | 0.209 | 270 nm | 18% | almost spherical |
| Example 9 | primary amination | 0.323 | 268 nm | 21% | almost spherical |
| Example 10 | quaternary amination | 0.178 | 265 nm | 22% | almost spherical |
| Example 11 | hydroxyl-ethylation | 0.256 | 263 nm | 24% | almost spherical |
| Example 12 | methylation | 0.972 | 264 nm | 20% | almost spherical |
| Example 13 | ethylation | 0.745 | 251 nm | 20% | almost spherical |
| Example 14 | crosslinking + carboxylation | 2.45 | 275 nm | 23% | almost spherical |
| Example 15 | primary amination + crosslinking | nitrogen content: 1.21% | 270 nm | 20% | almost spherical |
| Comparative Example 4 | underivatized (intact cellulose) | 0 | 261 nm | 18% | almost spherical |
| Comparative Example 5 | underivatized (intact cellulose) | 0 | 9.2 nm | 20% | almost spherical |
| Comparative Example 6 | underivatized (intact cellulose) | 0 | 521 nm | 26% | almost spherical |

When the obtained cellulose derivative fine particles and cellulose fine particles were evaluated for the dispersion stability, in all except for Comparative Example 3, a stable dispersion state was maintained without adding a surfactant or the like. In Comparative Example 3 where the particle diameter was large, precipitation was generated after standing still for several hours.

Example 16

<Production of Buffer Solution>

The following three kinds of buffer solutions were produced. The production was performed by a conventionally known method. The pH of the MES and Tris buffer solutions was adjusted using hydrochloride and sodium hydroxide, and the pH of the phosphate buffer solution was adjusted by controlling the amounts of disodium phosphate 12 hydrate and potassium dihydrogenphosphate. As for water, deionized water was used in all buffer solutions.

(1) MES buffer solution: pH-5.0, MES concentration of 50 mM (2) Phosphate buffer solution: pH=7.2, phosphate concentration of 50 mM (3) Tris buffer solution: pH-8.0, Tris concentration of 10 mM <Carbodiimide Activation of Carboxylated Cellulose Fine Particle>

2.5 Gram of the carboxylated cellulose fine particle dispersion liquid obtained in Example 1 was centrifuged at a speed of 15,000 rpm for 30 minutes. The precipitate was taken out by decantation, 0.5 g of the MES buffer solution was added, and the mixture was stirred to disperse carboxylated cellulose fine particles in the MES buffer solution.

1-Ethyl-3-(3-dimethylaminopropyl)carbodiimide hydrochloride (hereinafter referred to as “carbodiimide”) was dissolved in the MES buffer solution, thereby adjusting the carbodiimide concentration to 20 wt %, and a 0.5 g portion thereof was added to the carboxylated cellulose fine particle dispersion liquid. The reaction was allowed to proceed in an environment of 25° C. for 1 hour by using a constant temperature shaking bath, whereby carbodiimide-activated cellulose fine particles were prepared. After the completion of reaction, centrifugation was performed at a speed of 15,000 rpm for 30 minutes. The precipitate was taken out by decantation, 0.67 g of the phosphate buffer solution was added, and the mixture was stirred to disperse the carbodiimide-activated cellulose fine particles in the phosphate buffer solution.

<Binding of Anti-CRP Antibody to Carbodiimide-Activated Cellulose Fine Particle>

Furthermore, 75 μl of an aqueous anti-CRP antibody solution was added to the carbodiimide activated cellulose fine particle dispersion liquid, and the reaction was allowed to proceed in an environment of 25° C. for 20 hours by using a constant temperature shaking bath to prepare anti-CRP antibody-bound cellulose fine particles. After the completion of reaction, centrifugation was performed at a speed of 15,000 rpm for 30 minutes. The precipitate was taken out by decantation, and 2 g of the Tris buffer solution was added. An operation of performing centrifugation at a speed of 15,000 rpm for 30 minutes and taking out the precipitation by decantation was repeated two times, and the Tris buffer solution was added such that the particle concentration finally became 0.40 wt %. The obtained dispersion liquid was treated in an ultrasonic disperser (UH-50, manufactured by SMT Co., Ltd.) to prepare an anti-CRP antibody-loaded cellulose fine particle dispersion liquid.

<Calculation of Amount of Antibody Bound to Fine Particle>

Separately from the above, solutions in several kinds of concentrations were produced by adding an anti-CRP antibody to the phosphate buffer solution and measured for the absorbance at a fixed wavelength of 280 nm by using a spectral photometer (V-630, manufactured by JASCO Corporation), and a calibration curve of the anti-CRP antibody was prepared. The supernatant at the decantation above after the reaction with an anti-CRP antibody was measured by the same spectral photometer and when the amount of the anti-CRP antibody unloaded on the fine particle was weighed and the amount of the anti-CRP antibody loaded on the fine particle was back calculated therefrom, the amount of the anti-CRP antibody loaded was 180 μg per 1 mg of the particle.

<Latex Immunoassay>

Figure 2:
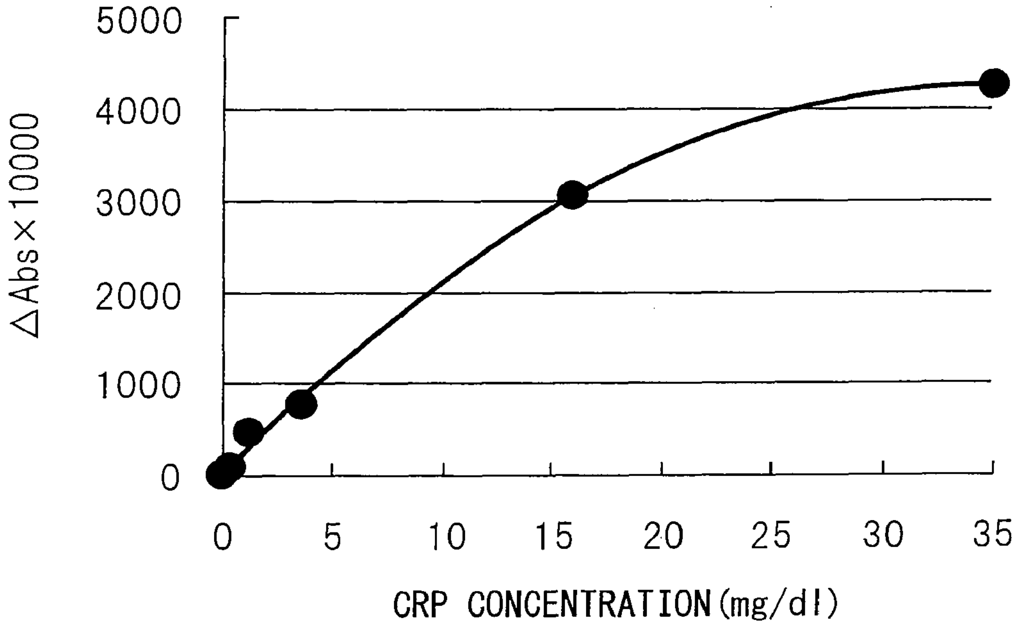
FIG. 2 is a view showing the evaluation results of the diagnostic reagent in Example 16 (abscissa: antigen concentration, ordinate: change of absorbance).

Using the anti-CRP antibody-loaded cellulose fine particle dispersion liquid obtained, the performance as a diagnostic reagent was evaluated. 6 Kinds of analytes in total, that is, 5 kinds of analytes each having a known antigen concentration and an analyte mixed with only the Tris buffer solution (corresponding to an antigen concentration of 0 mg/dl), were measured. FIG. 2 illustrates the results.

As apparent from FIG. 2, the anti-CRP antibody-loaded cellulose fine particle was changed in the degree of aggregation according to the amount of the CRP antigen and could be utilized as a diagnostic reagent.

Example 17

A anti-CRP antibody-loaded cellulose fine particle dispersion liquid was prepared in the same manner as in Example 16 except that after loading the anti-CRP antibody, a dispersion liquid having a fine particle concentration of 5.0 wt % was formed. The obtained dispersion liquid was put in a drop on a slide glass (MAS Coated Slide Glass, produced by Matsunami Glass Ind., Ltd.) and dried on standing in an environment of 25° C. for 24 hours. The drop-placed portion was observed by an electron microscope, as a result, it could be confirmed that the CRP antibody-loaded cellulose fine particles were fixed on the surface.

INDUSTRIAL APPLICABILITY

The cellulose derivative fine particle of the present invention has a small particle diameter and high hydrophilicity and therefore, can be stably dispersed without requiring a surfactant and the like. Also, various compounds can be loaded thereon. For example, the cellulose derivative fine particle can be utilized as a diagnostic reagent by loading an antibody thereon.

The invention claimed is:

1. A diagnostic reagent comprising a cellulose derivative fine particle, and a buffer solution, wherein the cellulose derivative fine particle comprises cellulose derivative with a part of hydroxyl groups of cellulose being substituted by a substituent, the cellulose derivative fine particle is water-insoluble, the average particle diameter of the cellulose derivative fine particle obtained by observation using electron microscope is from 9 to 1,000 nm, a coefficient of variation (CV) value is 30% or less, a ratio between major axis and minor axis of the cellulose derivative fine particle is 2.0 or less, the substitutent comprises any one or more members selected from the group consisting of a carboxyl group, an amino group, a quaternary ammonium group and a hydroxyalkyl group, the substitution degree of said substitution is 0.5 or less, and biomaterial is loaded on the cellulose derivative fine particle through chemical bonding or physical adsorption.

2. The diagnostic reagent according to claim 1, wherein the diagnostic reagent is for use in an immunoserological test.

3. The diagnostic reagent according to claim 1, wherein the biomaterial contains an antigen or antibody.

* * * * *